US012745969B2

(12) United States Patent
Maule et al.

(10) Patent No.: US 12,745,969 B2
(45) Date of Patent: Sep. 29, 2026

(54) COOLING SYSTEM FOR A COMPUTED TOMOGRAPHY (CT) IMAGING SYSTEM

(71) Applicant: GE Precision Healthcare LLC, Waukesha, WI (US)

(72) Inventors: Joseph Daniel Maule, Waukesha, WI (US); Samuel Edward Maule, Waukesha, WI (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 197 days.

(21) Appl. No.: 18/644,946

(22) Filed: Apr. 24, 2024

(65) Prior Publication Data

US 2025/0331782 A1 Oct. 30, 2025

(51) Int. Cl.
*A61B 6/03* (2006.01)
*A61B 6/00* (2024.01)

(52) U.S. Cl.
CPC ............ *A61B 6/035* (2013.01); *A61B 6/4435* (2013.01)

(58) Field of Classification Search
CPC ..... A61B 6/035; A61B 6/4435; A61B 6/4488; A61B 6/42; A61B 6/40; A61B 6/4476; A61B 6/4429; A61B 6/06; A61B 6/03; A61B 6/488; A61B 6/032; A61B 6/48; A61B 6/54; A61B 6/4494; A61B 6/44; A61B 6/0407; A61B 6/0492; A61B 6/04; A61B 6/545; A61B 6/542; A61B 6/405; A61B 6/58; A61B 6/469; A61B 6/463; A61B 6/467; A61B 6/465; A61B 6/5211; A61B 6/4035; A61B 6/547; A61B 6/461; A61B 6/0487; A61B 6/52; A61B 6/482; A61B 6/037; A61B 6/4241; A61B 6/4417; A61B 6/4291; A61B 6/4447;
(Continued)

(56) References Cited

U.S. PATENT DOCUMENTS 5,956,383 A * 9/1999 Kendall ................ H05G 1/025
378/141
7,283,607 B2 10/2007 Sommer
(Continued)

FOREIGN PATENT DOCUMENTS

| | | | |
|---|---|---|---|
| EP | 3984463 | A1 | 4/2022 |
| JP | 5324595 | B2 | 10/2013 |
| WO | 2021241595 | A1 | 12/2021 |

*Primary Examiner* — Irakli Kiknadze
(74) *Attorney, Agent, or Firm* — Daugherty & Del Zoppo, Co. LPA

(57) ABSTRACT

A computed tomography imaging system includes a gantry and a rotating frame rotatably supported in the gantry. The rotating frame includes an X-ray source and an X-ray radiation sensitive detector. The computed tomography imaging system further includes a plenum configured to hold pressurized air and a cooling system. The cooling system includes a heat exchanger configured to transfer heat from a coolant cooling at least one component carried by the rotating frame and a fan system configured to move cool air from the plenum to the heat exchanger and move heated air away from the heat exchanger. The cooling system further includes at least one of an air intake assembly configured to provide an air intake path for the cool air to the heat exchanger and an air exhaust assembly configured to provide an air exhaust path for the heated air.

20 Claims, 8 Drawing Sheets

(58) Field of Classification Search

CPC .. A61B 2560/0406; A61B 2018/00005; G01B 7/30; A61N 5/1049; A61N 2005/1059; A61N 2005/1061; G06N 3/09; G06N 3/08; G06N 3/0464; G16H 30/40; G01T 1/244; G01T 1/248; H05G 1/025; H05G 1/02; H01J 35/13; H01J 2235/1216; H01J 2235/1283; H01J 2235/1262; H01J 35/02; H01J 2235/12; Y10T 29/49716; F28D 1/024; F28D 1/047; F04D 29/601; F04D 25/166; F04D 29/582; G01N 23/046; G01N 2223/419; G01N 2223/31; G01N 2223/3103

USPC .............................. 378/4, 127, 199, 200, 141

See application file for complete search history.

(56) References Cited

U.S. PATENT DOCUMENTS

| | | | | |
|---|---|---|---|---|
| 10,213,175 | B2 | 2/2019 | Huang et al. | |
| 2004/0109538 | A1* | 6/2004 | McCarthy, Jr. ...... | A61B 6/4488 378/141 |
| 2009/0232281 | A1* | 9/2009 | Jimbo .................. | A61B 6/4488 378/199 |
| 2019/0166716 | A1 | 5/2019 | Li et al. | |

* cited by examiner

COOLING SYSTEM FOR A COMPUTED TOMOGRAPHY (CT) IMAGING SYSTEM

FIELD

The following generally relates to computed tomography (CT), and more particularly to a cooling system for a CT imaging system, and is also amenable to other imaging modalities and/or other systems.

BACKGROUND

A computed tomography (CT) imaging system generally includes a gantry that houses electrical and mechanical components utilized in the production, emission and detection of X-rays. For example, the gantry houses a stationary frame and a rotating frame, the rotating frame is rotatably supported via a bearing or the like within the gantry. Components such as an X-ray source, a high voltage generator, a data acquisition system, including an X-ray detector, etc. are carried on the rotating frame, and other components are carried on the stationary frame of the gantry. Some of these components produce heat that could be detrimental to components and/or quality of the imaging, if not dissipated, and some of these components are configured to operate within a certain temperature range and may not operate as expected outside of the temperature range.

An approach for reducing such heat includes employing a cooling system with the CT imaging system. An example of a suitable cooling system is a coolant-based cooling system configured to circulate a coolant, such as a liquid coolant (e.g., water, oil, etc.) and/or a gas coolant (e.g., air, etc.), about a component to transfer heat from the component to the coolant. The heated coolant is routed to a heat exchanger, which transfers heat out of the coolant. A fan is utilized to facilitate moving the heat dissipated by the heat exchanger away from the heat exchanger. The cooled coolant is then circulated again to remove heat, and this process continues to maintain a temperature in the gantry. FIGS. 1, 2, 3 and 4 collectively illustrate components of an example prior art cooling system.

FIG. 1 schematically illustrates a perspective view of a rotating frame 102 and a plenum 104. The plenum 104 is part of a gantry and is configured to hold pressurized air for cooling components, e.g., components carried by the rotating frame 102. The rotating frame 102 and the plenum 104 are separated by a gap 106. FIG. 2 schematically illustrates a front view of the rotating frame 102. In this example, the rotating frame 102 carries an X-ray source 202, a high voltage generator 204, a data acquisition system 206, etc. The rotating frame 102 further carries an X-ray source cooling system 208, a high voltage generator cooling system 210, and a data acquisition system cooling system 212.

The X-ray source cooling system 208 includes at least a heat exchanger 214 and a fan system 216, the high voltage generator cooling system 210 includes at least a heat exchanger 218 and a fan system 220, and the data acquisition system cooling system 212 includes at least a heat exchanger 222 and a fan system 224. FIG. 3 schematically illustrates a top down view of a portion of the rotating frame 102 and the plenum 104 in connection with the heat exchanger 214 and the fan system 216 for the X-ray source cooling system 208. FIG. 4 schematically illustrates the heat exchanger 214 for the X-ray source cooling system 208 in fluid communication with the X-ray source 202 via a line 302 and a pump 304 to move the coolant to the X-ray source 202 and via a line 306 to move coolant from the X-ray source 202 to the heat exchanger 214.

With reference to FIGS. 1, 2, 3 and 4, in general, the pump 304 pumps coolant to the X-ray source 202 via the line 302. The coolant is circulated in connection with the X-ray source 202, and heat produced by the X-ray source 202 is transferred to and carried away by the coolant. The coolant is routed from the X-ray source 202 to the heat exchanger 214 of the X-ray source cooling system 208. The heat exchanger 214 is configured to transfer heat from the coolant to the surrounding air. The fan system 216 of the X-ray source cooling system 208 draws cooler air from the plenum 104 to the heat exchanger 214 to remove heat and expel hotter air produced by the transfer of heat from the coolant to the air. The cooled coolant is then likewise used again to remove heat produced by the X-ray source 202.

Unfortunately, during scanning that requires rotating the rotating frame 102, the rotation of the rotating frame creates turbulent air flow, which can hinder the fan system 216 from pulling cooler air from the plenum 104 and/or pushing hotter air away from the heat exchanger 214. As a consequence, the fan system 216 may need to operate at a higher speed than desired based on the rotational speed of the rotating frame 102 to maintain a predetermined temperature of the X-ray source 202, other component and/or an internal environment of the gantry, and a higher fan speed may result in additional audible noise, power consumption and/or dissipated heat from the fan system 216, and/or a reduction of a lifespan of the fan system 216, which may increase overall imaging system cost over a lifetime of the imaging system.

In view of at least the foregoing, there is an unresolved need for an improved approach for reducing audible noise from a component of an imaging and/or other system.

SUMMARY

Aspects described herein address the above-referenced problems and others. This summary introduces concepts that are described in more detail in the detailed description. It should not be used to identify essential features of the claimed subject matter, nor to limit the scope of the claimed subject matter.

In one aspect, a computed tomography imaging system includes a gantry and a rotating frame rotatably supported in the gantry. The rotating frame includes an X-ray source configured to emit X-ray radiation that traverses an examination region and an X-ray radiation sensitive detector disposed opposite the X-ray source and configured to detect X-ray radiation traversing the examination region and generate signals indicative of the detected X-ray radiation. The computed tomography imaging system further includes a plenum configured to hold pressurized air and a cooling system. The cooling system includes a heat exchanger configured to transfer heat from a coolant cooling at least one component carried by the rotating frame and a fan system configured to move cool air from the plenum to the heat exchanger and move heated air away from the heat exchanger. The cooling system further includes at least one of: an air intake assembly configured to provide an air intake path for the cool air to the heat exchanger and an air exhaust assembly configured to provide an air exhaust path for the heated air.

In another aspect, a computer-implemented method includes receiving, at an air intake assembly of a cooling system of a computed tomography imaging system, turbulent air produced in response to rotating a rotating frame of a gantry of the computed tomography imaging system. The computer-implemented method further includes opening an elongated louver of the air intake assembly with the turbulent air. The open elongated louver provides an air intake scoop. The computer-implemented method further includes routing, with the air intake scoop and a fan system of the computed tomography imaging system, air from a plenum of the computed tomography imaging system to a heat exchanger of the computed tomography imaging system, providing a first flow of air.

In another aspect, a computer-implemented method includes receiving, at an air intake assembly of the cooling system, turbulent air produced in response to rotating the rotating frame of the gantry of the computed tomography imaging system. The computer-implemented method further includes automatically opening an elongated louver of the air intake assembly with the turbulent air. The open elongated louver provides an air intake scoop. The computer-implemented method further includes routing, with the air intake scoop and a fan system disposed in of the computed tomography imaging system, air from a plenum of the computed tomography imaging system to a heat exchanger of the computed tomography imaging system.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings in which like references indicate similar elements.

DETAILED DESCRIPTION

Embodiments of the present disclosure will now be described, by way of example, with reference to the figures, in which a system, a method and/or a computer readable medium includes instructions for reducing heat produced by one or more components of an imaging system includes employing an air intake assembly with a cooling system for a component that facilitates moving cooling air from a plenum into a fan intake of the cooling system, and, additionally, or alternatively, employing an air exhaust assembly with the cooling system for the component that facilitates moving heated air away from the cooling system.

As discussed above, a CT imaging system includes components that produce heat that could be detrimental to components and/or quality of the imaging, if not dissipated, and some of these components are configured to operate within a certain temperature range and may not operate as expected outside of the certain temperature range, and existing approaches for removing heat during rotation of the rotating frame are susceptible to being hindered by turbulent air flow resulting from the rotating frame, which may result in higher fan speeds than desired to maintain a temperature, and a higher fan speed may result in additional audible noise, power consumption and/or heat dissipated from the fan system, which may reduce a lifespan of the fan system, which may increase overall cost over a lifetime of the imaging system.

With the approach described herein, when the rotating frame rotates, turbulent air flow resulting from the rotating frame opens an air intake scoop of the air intake assembly, which provides an efficient air intake path for cooling air from the plenum to the heat exchanger of the cooling system, and can mitigate at least the above-noted shortcomings associated with the intake air resulting from the turbulent air flow from the rotating frame, and/or an air exhaust scoop of the air exhaust assembly provides an efficient air exhaust path for heated air from the heat exchanger to the surrounding environment, which can mitigate at least the above-noted shortcomings associated with expelling the heated air resulting from the turbulent air flow from the rotating frame.

Figure 1:
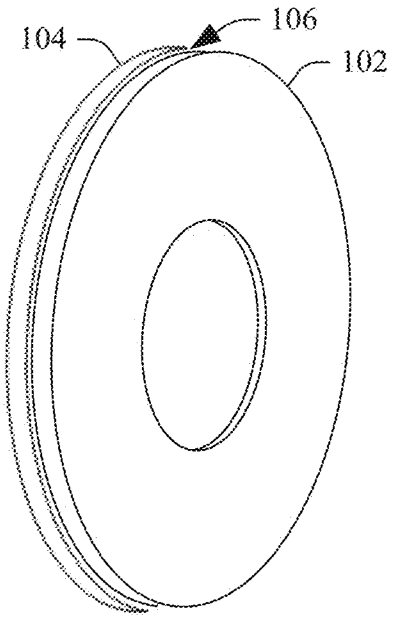
FIGURE 1 (PRIOR ART)
FIG. 1 schematically illustrates a perspective view of a prior art rotating frame and plenum.
Figure 2:
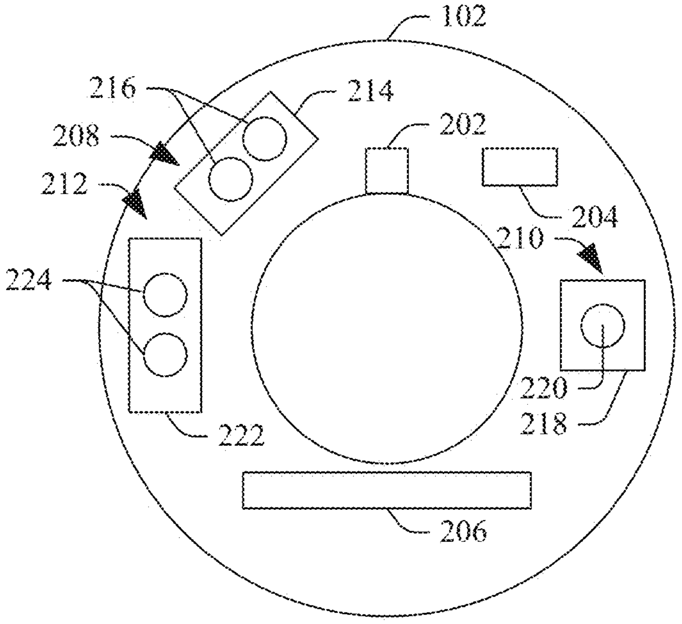
FIGURE 2 (PRIOR ART)
FIG. 2 schematically illustrates a front view of the rotating frame of FIG. 1 with certain components and prior art cooling systems, including heat exchangers for the components.
Figure 3:
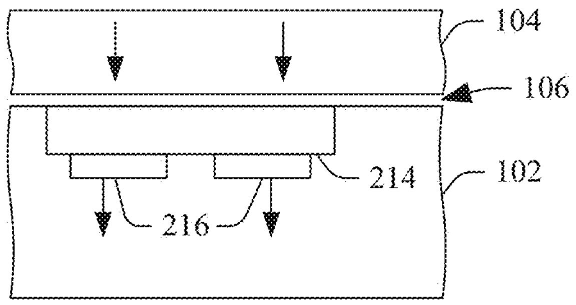
FIGURE 3 (PRIOR ART)
FIG. 3 schematically illustrates a top down view of a portion of the rotating frame and the plenum of FIGS. 1 and 2 in connection with a heat exchanger and fan system of a prior art X-ray source cooling system.
Figure 4:
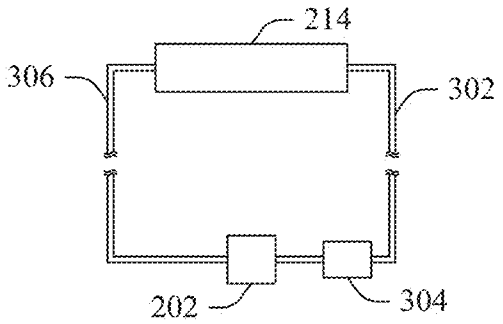
FIGURE 4 (PRIOR ART)
FIG. 4 schematically illustrates the heat exchanger for the prior art X-ray source cooling system in fluid communication with the X-ray source via a line and a pump to move the coolant to the X-ray source and via a line to move coolant from the X-ray source to the heat exchanger.
Figure 5:
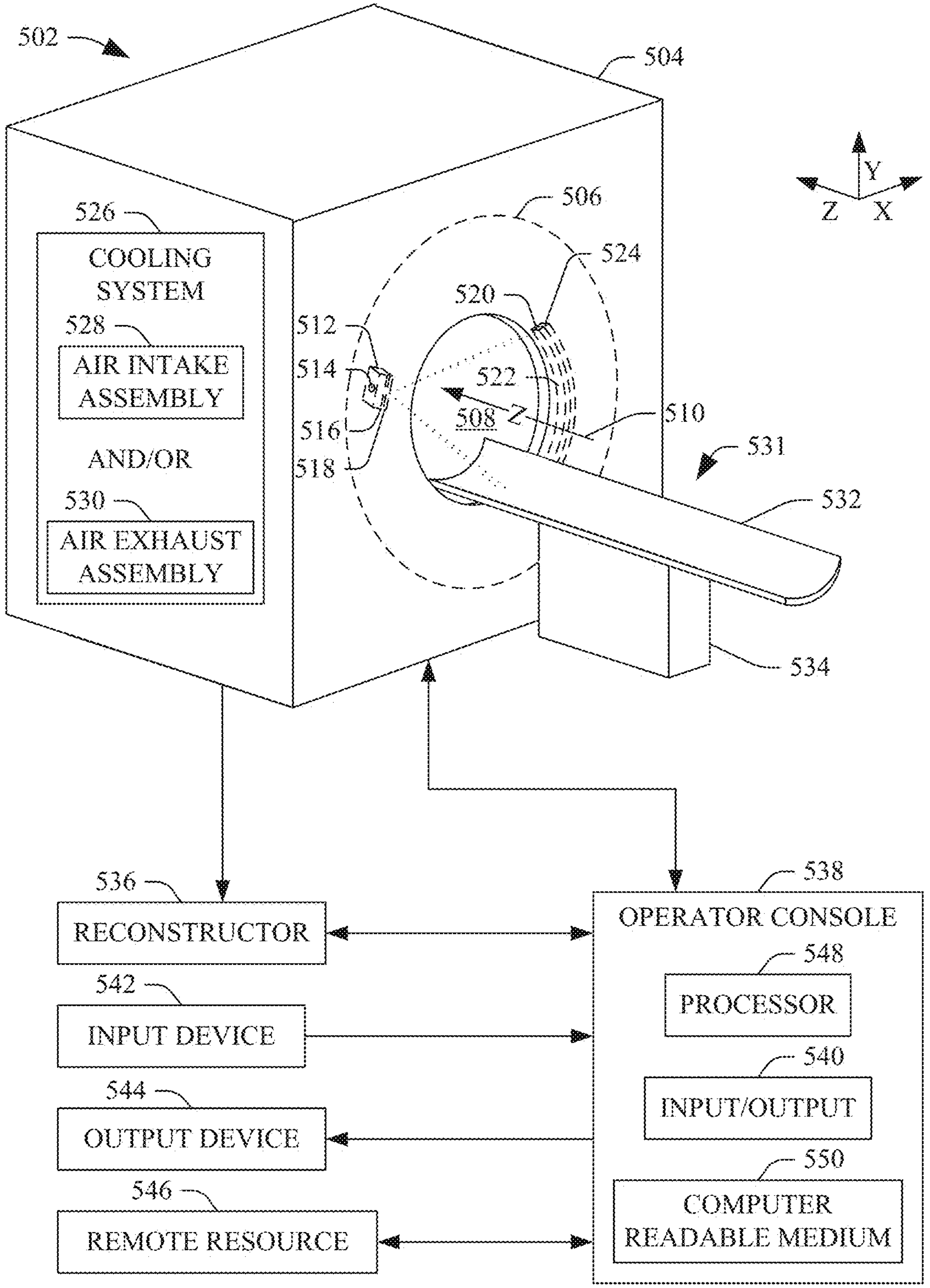
FIG. 5 schematically illustrates a non-limiting example of an imaging system configured for computed tomography imaging, in accordance with an embodiment(s) herein.

Initially referring to FIG. 5, a non-limiting example of an imaging system 502 such as a computed tomography (CT) imaging system is schematically illustrated. The imaging system 502 includes a gantry 504. In some instances, the gantry 504 is configured to tilt. The imaging system 502 further includes a rotating frame 506. The rotating frame 506 is rotatably supported in the gantry 504, e.g., via a bearing or the like, and is configured to rotate around an examination region 508 about a rotational or z-axis 510. The rotating frame 506 carries components such as an X-ray source, a high voltage generator, a data acquisition system, including an X-ray detector, etc.

Figure 6:
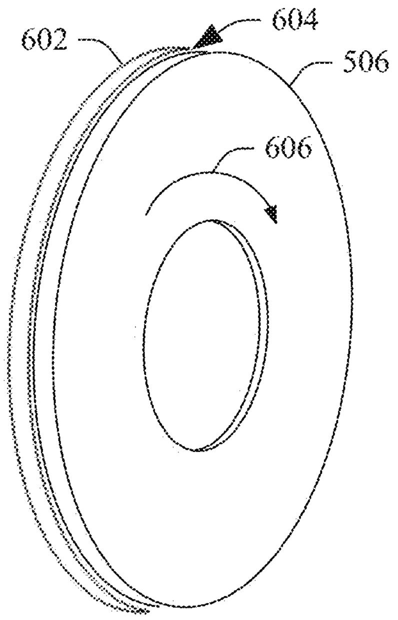
FIG. 6 schematically illustrates a non-limiting example of a perspective view of a of a rotating frame and a plenum of the imaging system of FIG. 5, in accordance with an embodiment(s) herein.

Briefly turning to FIG. 6, a perspective view shows the rotating frame 506 disposed adjacent to a plenum 602 of the gantry 504, separated from the plenum 602 by a gap 604 is schematically illustrated. The rotating frame 506 is configured to rotate in a direction 606, which is a clockwise direction looking into FIG. 6. The plenum 602 remains stationary when the rotating frame 506 is at a static position and when the rotating frame 506 is rotating. The plenum 602 is configured to hold pressurized air. As described in greater detail below, the pressurized air, in one instance, is employed to facilitate removal of heat in connection with certain components, e.g., temperature sensitive components carried by the rotating frame 506, etc. Returning to FIG. 5, a gantry controller is configured to control rotation of the rotating frame 506 and, if configured to tilt, tilting of the gantry 504.

An X-ray source assembly 512 is supported by the rotating frame 506 and rotates in coordination with the rotating frame 506. The X-ray source assembly 512 includes an X-ray source 514 such as an X-ray tube. The X-ray source 514 is configured to emit X-ray radiation having an energy in the X-ray diagnostic range (e.g., 20 keV to 150 keV). The X-ray assembly 512 may further include or is coupled to a filter 516 that characterizes a radiation dose profile and/or a collimator 518 that shapes the X-ray radiation to form a generally fan, wedge, cone, etc. shaped beam that traverses the examination region 508. An X-ray controller is configured to control components of the X-ray assembly 512 such as radiation emission of the X-ray source 514, the collimator 518, etc.

An X-ray radiation sensitive detector array 520 includes a one- or two-dimensional (1-D or 2-D) array of rows of X-ray radiation sensitive detector elements 522 and is supported by the rotating frame 506 along an arc opposite the X-ray source 514, across the examination region 508. Each X-ray radiation sensitive detector element is in electrical communication with a data acquisition 524. The detector elements include an indirect conversion detector such as a scintillator/photodiode detector and/or a direct conversion detector such as a Cadmium Telluride (CdTe), a Cadmium Zinc Telluride (CZT), etc. detector. A data acquisition electronics controller controls the data acquisition 524.

Figure 7:
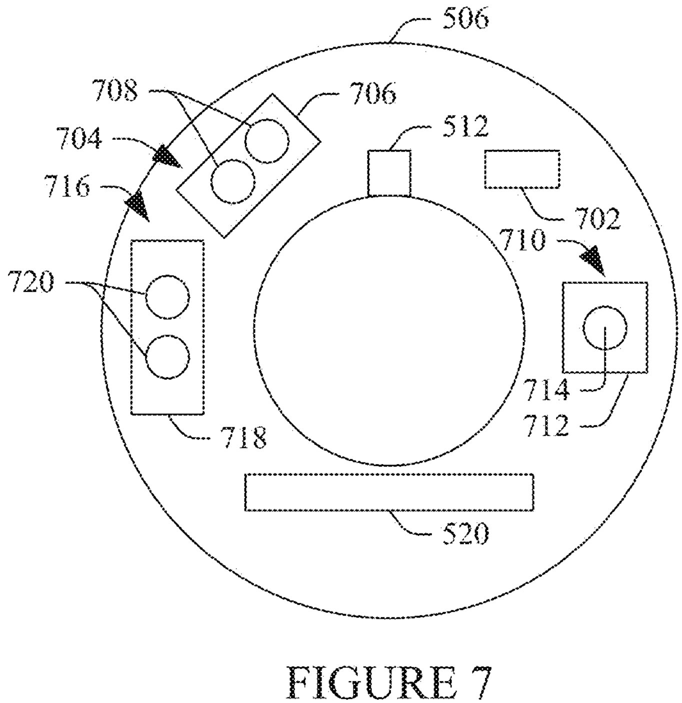
FIG. 7 schematically illustrates a front view of the rotating frame of FIG. 6 showing a portion of the cooling system in connection with example components cooled with the cooling system, in accordance with an embodiment(s) herein.

A cooling system 526 is configured to cool at least one component and/or an atmosphere in the gantry 504. Briefly turning to FIG. 7, a front view of the rotating frame 506 showing a portion of the cooling system 526 in connection with the X-ray source 514, the radiation sensitive detector array 520, a high voltage generator 702 is schematically illustrated. The cooling system 526 includes one or more of an X-ray source cooling system 704 with at least a heat exchanger 706 and a fan system 708, a high voltage generator cooling system 710 with at least a heat exchanger 712 and a fan system 714, and a data acquisition system cooling system 716 with at least a heat exchanger 718 and a fan system 720. The fan system 708, 714 and/or 720 can include one or more fans. In another example, the cooling system 526 includes cooling for other and/or different components of the imaging system 502.

An example of a cooling system for an X-ray tube is described in U.S. Pat. No. 7,236,571 B2 to General Electric Co., granted Apr. 6, 2007, and entitled "Liquid cooled thermal control system for an imaging detector," the entirety of which is incorporated herein by reference. With this configuration, the cooling system includes a pump, a heat exchanger, a fluid channel, and fluid conduits. During imaging, heat produced by the X-ray tube is removed with a cooled fluid routed, via the pump and the fluid channel, in close proximity to a heat producing portion of the X-ray tube, and the heated fluid is routed, via the pump and the fluid conduits, to a heat exchanger, which removes heat from the fluid, e.g., by forced air cooling where a fan moves air over the heat exchanger. Other X-ray tube cooling systems are also contemplated herein.

An example of a cooling system for an X-ray detector is described in U.S. Pat. No. 8,699,660 B2 to General Electric Co., granted Apr. 4, 2014, and entitled "Systems and apparatus for integrated X-Ray tube cooling," the entirety of which is incorporated herein by reference. With this configuration, the cooling system includes cooling channels (having a cooling fluid flowing therethrough) in thermal communication with the X-ray detector to transfer heat from the X-ray detector to the cooling fluid, a pump to control a flow of the cooling fluid, and a hot channel configured to route heated cooling fluid to a heat exchanger, which is configured to remove heat from the heated cooling fluid. Other detector cooling systems are also contemplated herein.

Returning to FIG. 5, the cooling system 526 includes an air intake assembly 528 and/or an air exhaust assembly 530. The air intake assembly 528 is configured to move cooling air from the plenum 602 into a fan of at least one of the fan systems 708, 714, 720, etc. in connection with at least one of the X-ray source cooling system 704, the high voltage generator cooling system 710, the data acquisition cooling system 716, etc. As described in greater detail below, when rotating the rotating frame 506, turbulent air flow opens the air intake assembly 528, which provides an air intake path for cooling air from the plenum to the heat exchanger 706, 712, 718, etc., and/or the air exhaust assembly 530 provides an air exhaust path to move heated air away from the heat exchanger 706, 712, 718, etc.

It is to be appreciated that the approach described herein can improve an efficiency with drawing in cooling air and/or expelling heated air, relative to a configuration in which the air intake assembly 528 and/or the air exhaust assembly 530 are omitted. For example, a speed of an air intake fan can be maintained and/or reduced while achieving a same desired temperature of components therein and/or an environment therein, relative to a configuration omitting the air intake assembly 528 and/or the air exhaust assembly 530. In one instance, reducing the intake fan speed may further reduce audible noise, power consumption and/or an amount of heat produced by the fan system 708, 714, 720 and/or etc., which may increase a lifespan of the air intake fan and/or reduce an overall cost of the imaging system cost over a lifetime of the imaging system.

Returning to FIG. 5, a subject/object support 531 includes a tabletop 532 moveably coupled to a frame/base 534. In one instance, the tabletop 532 is slidably coupled to the frame/base 534 via a bearing or the like, and a drive system (not visible) including a controller, a motor, a lead screw, and a nut (or other drive system) translates the tabletop 532 along the frame/base 534 into and out of the examination region 508. The tabletop 532 is configured to support an object or subject in the examination region 508 for loading, scanning, and/or unloading the subject or object. A table controller controls the drive system.

For a helical scan, the rotating frame 106 506 rotates in the direction 606 (FIG. 6) in coordination with the tabletop 532 moving along the Z-axis 510, and active X-ray detector elements 522 of the X-ray radiation sensitive detector 524 detect X-ray radiation over consecutive arc segments (integration periods) each revolution and generate respective signals. For an axial (step and shoot) scan, the tabletop 532 is positioned at a static position for each integration period and moves between integration periods. For each arc segment, the data acquisition electronics 524 processes each signal and generates projection data.

A reconstructor 536 reconstructs the projection data and generates volumetric (3-D) image data for a helical scan and/or individual axial (2-D) images for an axial step and shoot scan (which can be used in combination to generate volumetric image data). The volumetric image data and/or 2-D slices thereof, and/or the individual axial images can be visually presented, filmed, etc. Examples of suitable reconstruction algorithms include filtered back projection (FBP), advanced statistical iterative reconstruction (ASIR), conjugate gradient (CG), maximum likelihood expectation maximization (MLEM), model-based iterative reconstruction (MBIR), and/or other reconstruction algorithm.

A computing system 538 serves as an operator console of the system 502. The computing system 538 may include a computer, a workstation, etc. The computing system 538 includes input/output (I/O) 540. An input device 542 includes a keyboard, mouse, touchscreen, microphone, etc. The input device 542 is in electrical communication with the computing system 538 through the I/O 540 and/or otherwise. An output device 544 includes a human readable device such as a display monitor or the like. The output device 544 is in electrical communication with the computing system 538 through the I/O 540 and/or otherwise.

A remote resource 546 includes one or more of a server, a workstation, a Radiology Information System (RIS), a Hospital Information System (HIS), an electronic medical record (EMR), a Picture Archiving and Communications System (PACS), one or more other CT scanners, cloud processing resources (which includes shared remote data storage and/or computing power, including processing resources distributed over multiple locations/data centers), etc. The remote resource 546 is in electrical communication with the computing system 538 through the I/O 540 and/or otherwise.

The computing system 538 further includes at least one processor 548 such as a microprocessor (μP), a central processing unit (CPU), graphics processing unit (GPU), etc., and computer readable medium 550, which includes non-transitory medium and excludes transitory medium (signals, carrier waves, and the like). The computer readable medium 550 is embedded or encoded with computer executable instructions, e.g., application software, which allows a user to select a protocol, start scanning, etc. In one instance, the protocol indicates imaging related parameters such as a rotating frame 506 rotational speed, where the intake fan speed of the cooling system 526 is set according to the rotating frame 506 rotational speed.

As briefly discussed herein, in one instance the cooling system 526 includes the air intake assembly 528. FIGS. 8, 9, 10, 11 and 12 schematically illustrates an example of the air intake assembly 528. For sake of brevity and clarity, the example air intake assembly 528 is described in connection with the X-ray source cooling system 704. However, it is to be understood that description further applies to cooling systems for other components of the imaging system 502, e.g., the high voltage generator cooling system 710, the data acquisition system cooling system 716, etc.

Figure 8:
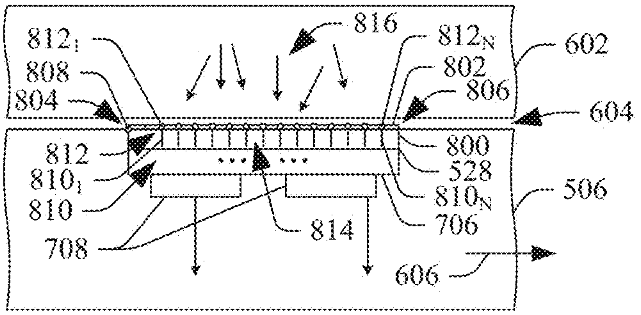
FIG. 8 schematically illustrates a non-limiting example of a side view of a portion of the cooling system in connection with the rotating frame and plenum with the air intake assembly of the cooling system in a closed position, in accordance with an embodiment(s) herein.
Figure 9:
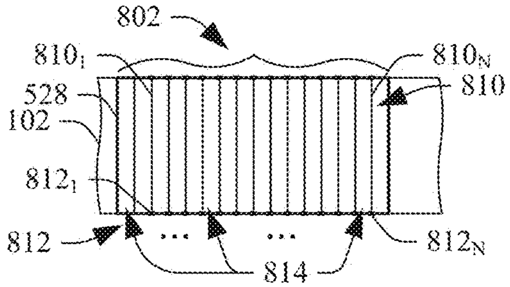
FIG. 9 schematically illustrates a non-limiting example of a top down view of into the air intake assembly illustrated in FIG. 8, in accordance with an embodiment(s) herein.

Initially referring to FIGS. 8 and 9, the rotating frame 506 is at a static location and not rotating. The direction of rotation 606, when the rotating frame 506 rotates, is shown left to right. The air intake assembly 528 is disposed adjacent to the heat exchanger 706 on the rotating frame 506. The air intake assembly 528 can be partially in the gap 604 (as illustrated) or entirely outside of the gap 604. The air intake assembly 528 includes a first portion 800 and a second portion 802. The first portion 800 serves as a shoot and is referred to herein as the shoot 800, and second portion 802 serves as part of a scoop and is referred to herein as the elongated louver 802.

The elongated louver 802 includes a first end region 804 and a second end region 806, located opposite the first end region 804 on a long axis of the elongated louver 802. In this example, the end region 806 is a leading end of the elongated louver 802 in that the end region 806 leads the elongated louver 802 relative to the rotational direction 606 of the rotating frame 506, and the end region 804 is a lagging end of the elongated louver 802 in that the end region 806 lags or follows the (leading) end region 806 of the elongated louver 802 relative to the rotational direction 606 of the rotating frame 506.

The air intake assembly 528 further include a mechanical bearing 808 pivotably attached to the end region 804 and fixedly attached to the shoot 800 at a static position. The first end region 804 is configured to pivot with one degree of freedom between a position at which the elongated louver 802 is generally parallel to the heat exchanger 706 and covers the heat exchanger 706 and one or more other positions where the (leading) end region 806 pivots away from the heat exchanger 706 and towards the plenum 602, which will be described in greater detail below. An example of the mechanical bearing 808 is a hinge or the like.

The elongated louver 802 further includes a plurality of slats 810, including a first slat 8101, . . . , an Nth slat 810N, where N is an integer equal to or greater than one. The elongated louver 802 further includes a plurality of pivot joints 812, including a first pivot joint 8121, . . . , an Nth pivot joint 812N. Each of the slats 810 is pivotably coupled to a corresponding pivot joint of the pivot joints 812. The slats 810 are configured to be in a normally open position when the rotating frame 506 is at a static location and not rotating, as shown. In this position, the slats 810 provide material free channels 814 for air 816 to flow from the pressurized plenum 602 to the heat exchanger 706.

Figure 10:
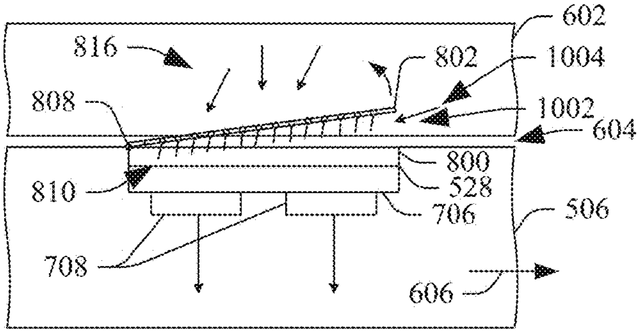
FIG. 10 schematically illustrates a non-limiting example of the side view of FIG. 8 with the air intake assembly of the cooling system in a partially open position, in accordance with an embodiment(s) herein.

FIG. 10 schematically illustrates the elongated louver 802 in a partially open/closed position. When the rotating frame 506 rotates in the direction 606, turbulent air flow resulting from the rotating frame 506 causes the (leading) end region 806 to lift away from the heat exchanger 706 and towards the plenum 602, the elongated louver 802 to pivot about the mechanical bearing 808, and the slats 810 begin to close. This creates an air path 1002, and the elongated louver 802 scoops air 1004 from the plenum 602 into the shoot 800 and to the heat exchanger 706.

In one instance, FIG. 10 represents a transition position between a fully closed position and a fully open position. In other words, the elongated louver 802 is either in the fully closed position or the fully open position, and FIG. 10 represents a snapshot in time during the transition. In another instance, the FIG. 10 represents an intermediate position of a set of intermediate positions, each corresponding to a different rotating frame 506 rotational speed. That is, different rotational speeds create different turbulent flow, and the extent the elongated louver 802 pivots depends on the rotational speed.

Figure 11:
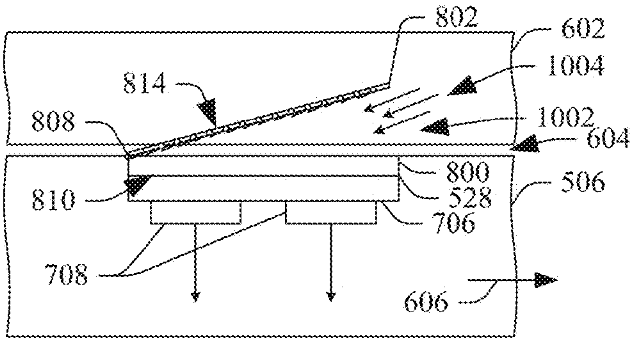
FIG. 11 schematically illustrates a non-limiting example of the side view of FIG. 8 with the air intake assembly of the cooling system in a fully open position, in accordance with an embodiment(s) herein.
Figure 12:
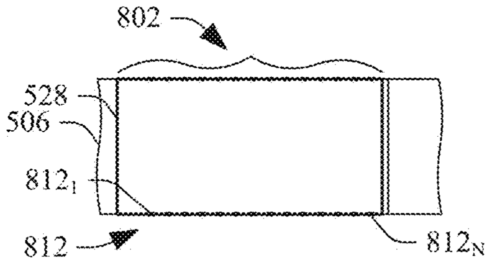
FIG. 12 schematically illustrates a non-limiting example of a top down view of the air intake assembly illustrated in FIG. 11, in accordance with an embodiment(s) herein.

FIG. 11 schematically illustrates the elongated louver 802 in a fully open position. In this position, the elongated louver 802 pivots further, the slats 810 fully close, which closes the channels 814, preventing air from moving from the plenum 602, through the channels 814, to the heat exchanger 706, and the air path 1002 widens. The elongated louver 802 scoops the air 1004 from the plenum 602 into the shoot 800 and to the heat exchanger 706. FIG. 12 schematically illustrates a top down view into the elongated louver 802 with all the slats 810 closed and no channels for the air 816.

With reference to FIGS. 8, 9, 10, 11 and 12, the air path 1002 provides a path that routes and/or forces the air 1004 in the plenum 602 to the heat exchanger 706, especially when all of the slates 810 are completely closed. This mitigates the turbulent air flow hindering the fan system 708 from drawing the air 816 through the channels 814 as the channels either are not utilized or are only partially relied on and the turbulent air flow does not hinder the flow of the 1004 through the path 1002 to the heat exchanger 706. This can mitigate at least the above-noted shortcomings associated with drawing cooling air in the presence of the turbulent air flow from the rotating frame 506.

In one instance, this can also improve an efficiency with drawing in cooling air, relative to a configuration in which the air intake assembly 528 is omitted. For example, a speed of an air intake fan can be maintained and/or reduced while achieving a same desired temperature of components therein and/or an environment therein, relative to a configuration omitting the air intake assembly 528. In one instance, reducing the intake fan speed may further reduce audible noise, power consumption and/or an amount of heat produced by the air intake fan, which may increase a lifespan of the air intake fan and/or reduce an overall cost of the imaging system cost over a lifetime of the imaging system.

Figure 13:
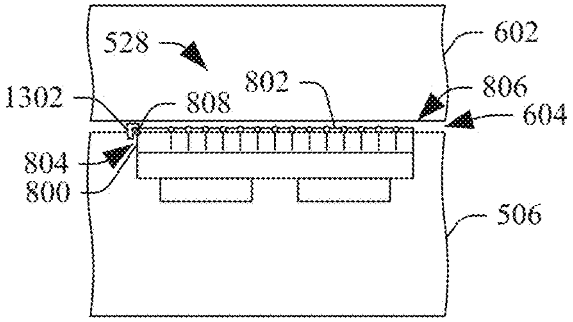
FIG. 13 schematically illustrates a non-limiting example in which the air intake assembly includes a mechanical stop and the elongate louver is in the closed position, in accordance with an embodiment(s) herein.
Figure 14:
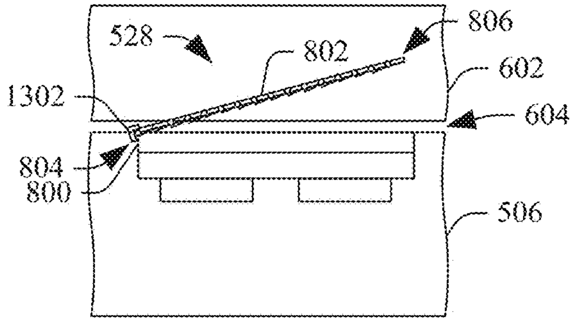
FIG. 14 schematically illustrates the non-limiting example of FIG. 13 with the elongate louver in the open position, in accordance with an embodiment(s) herein.

FIGS. 13 and 14 schematically illustrate a non-limiting example in which the air intake assembly 528 further includes a mechanical stop 1302 configured to restrict the pivot motion of the mechanical bearing 808 and hence the movement of the elongated louver 802.

In FIG. 13, the elongated louver 802 is in the fully closed position, and in FIG. 14, the elongated louver 802 is in the fully open position. With reference to FIGS. 13 and 14, the mechanical stop 1302 is disposed on the elongated louver 802. In this example, the mechanical stop 1302 is “L” shaped. The horizontal leg of the “L” is disposed at the (rear) end region 804 of the elongated louver 802 over the mechanical bearing 808. The horizontal leg of the “L” protrudes out and away from the elongated louver 802. The vertical leg of the “L” extends therefrom toward the rotating frame 506 and away from the plenum 602, behind the mechanical bearing 808 and the shoot 800.

In the closed position (FIG. 13), the free end of the vertical leg of the “L” is separated from the shoot 800 by a gap, which allows the elongated louver 802 to pivot about the mechanical bearing 808 and open. In the fully open position (FIG. 14), the free end of the vertical leg of the “L” is in physical contact with shoot 800, which prevents the elongated louver 802 from pivoting any further about the mechanical bearing 808. In one instance, the mechanical stop 1302 prevents the elongated louver 802 from pivoting to a position at which the elongated louver 802 could not return to the closed position by itself should the rotating frame 506 slow down or stop rotating.

In FIGS. 13 and 14, the mechanical stop 1302 pivots with the elongated louver 802. In another instance, the mechanical stop 1302 is disposed at the shoot 800, behind and below the mechanical bearing 808, and is a stationary member. In this position, the mechanical stop 1302 does not pivot with the elongated louver 802. The elongated louver 802 pivots as disclosed herein until the elongated louver 802 physically contacts the mechanical stop 1302, which prevents the elongated louver 802 from pivoting any further about the mechanical bearing 808. In another instance, the mechanical stop 1302 is otherwise shaped and/or located.

Figure 15:
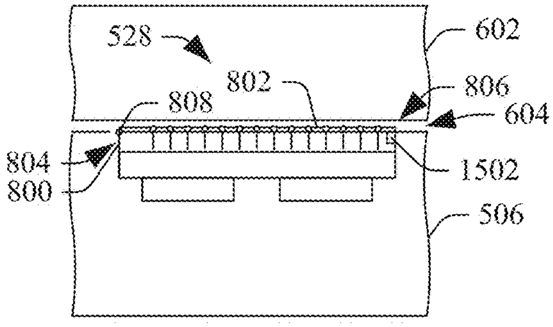
FIG. 15 schematically illustrates a non-limiting example in which the air intake assembly includes an elastic member and the elongate louver is in the closed position, in accordance with an embodiment(s) herein.
Figure 16:
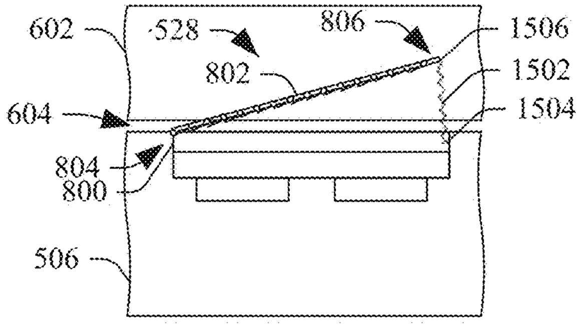
FIG. 16 schematically illustrates the non-limiting example of FIG. 15 with the elongate louver in the open position, in accordance with an embodiment(s) herein.

FIGS. 15 and 16 schematically illustrate a non-limiting example in which the air intake assembly 528 includes an elastic member 1502 configured to hold the elongated louver 802 in a normally closed position when the rotating frame 506 is not rotating, restrict the pivot motion of the mechanical bearing 808 when the rotating frame 506 is rotating, and/or facilitate returning the elongated louver 802 from the open position to the closed position in response to the rotating frame 506 slowing down and/or stopping rotating.

In FIG. 15, the elongated louver 802 is in the fully closed position, and in FIG. 16, the elongated louver 802 is in the fully open position. With reference to FIGS. 15 and 16, the elastic member 1502 is disposed on the (leading) end region 806. A first end 1504 of the elastic member 1502 is disposed in connection with the shoot 800. A second end 1506 of the elastic member 1502 is affixed to the (leading) end region 806 of the elongated louver 802. In this example, the elastic member 1502 is a preloaded spring, configured to operate with a tension load.

In the closed position (FIG. 15), the pre-loaded tension of the elastic member 1502 maintains the elongated louver 802 in the closed position. In the fully open position (FIG. 16), the elastic member 1502 stretches in response to a certain load from the air flow, allowing the elongated louver 802 to pivot and open and limiting the pivot motion of the elongated louver 802. During a transition from the open position to the closed position, the pre-loaded tension of the elastic member 1502 facilitates closing the elongated louver 802.

Figure 17:
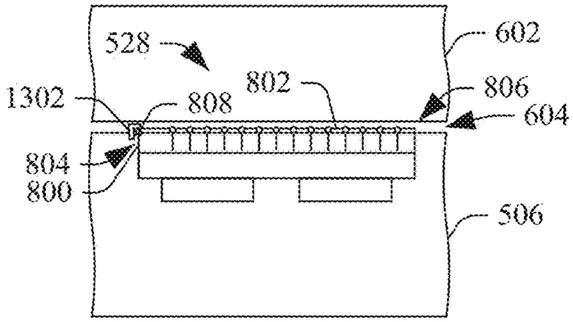
FIG. 17 schematically illustrates a non-limiting example in which the air intake assembly includes the mechanical stop of FIGS. 13 and 14 and the elastic member of FIGS. 15 and 16, and the elongate louver is in the closed position, in accordance with an embodiment(s) herein.
Figure 18:
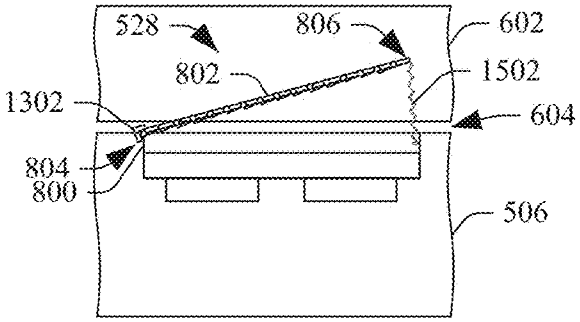
FIG. 18 schematically illustrates the non-limiting example of FIG. 17 with the elongate louver in the open position, in accordance with an embodiment(s) herein.

FIGS. 17 and 18 schematically illustrate a combination of the examples illustrated in FIGS. 13, 14, 15 and 16. That is, the example in FIGS. 17 and 18 includes both the mechanical stop 1302 and the elastic member 1502. In this example, the elastic member 1502 is configured to hold the elongated louver 802 in a normally closed position when the rotating frame 506 is not rotating, the mechanical stop 1302 restricts the pivot motion of the movement of the elongated louver 802 when the rotating frame 506 is rotating, and the elastic member 1502 facilitates returning the elongated louver 802 from the open position to the closed position in response to the rotating frame 506 slowing down and/or stopping rotating.

Figure 19:
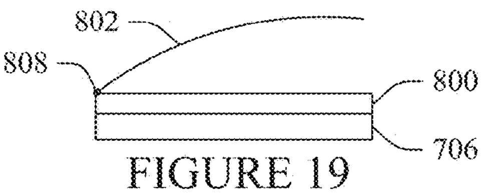
FIG. 19 schematically illustrates another example of the elongate louver having an arc shape, in accordance with an embodiment(s) herein.
Figure 20:
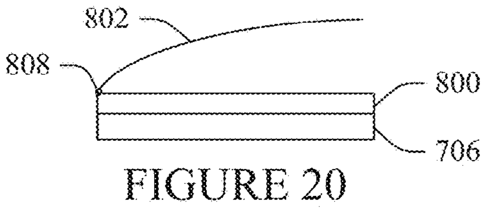
FIG. 20 schematically illustrates another example of the elongate louver having an elliptical shape, in accordance with an embodiment(s) herein.

In FIGS. 13, 14, 15, 16, 17 and 18, the example elongated louver 802 is linear. In another example, the elongated louver 802 is curve shaped. Examples of curves include an arc shape, an elliptical shape, a parabolic shape, etc. FIG. 19 schematically illustrates examples of an arc shaped elongated louver 802. FIG. 20 schematically illustrates an example of an elliptical shaped elongated louver 802.

Figure 21:
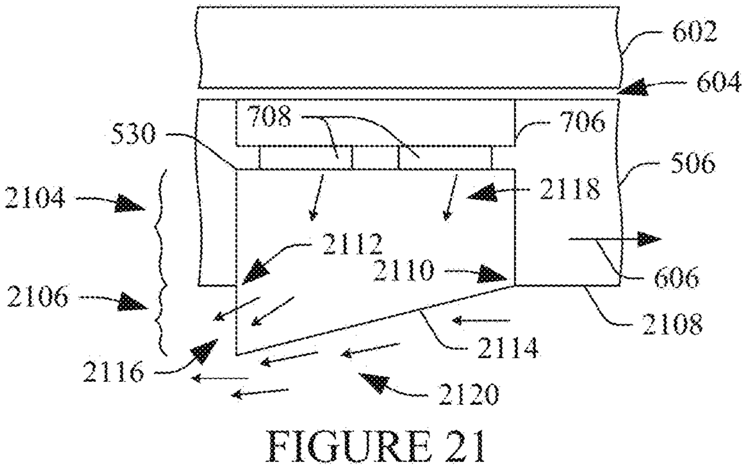
FIG. 21 schematically illustrates an example of the air exhaust assembly with a linear air scoop side, in accordance with an embodiment(s) herein.

As briefly discussed herein, in one instance the cooling system 526 additionally, or alternatively, includes an air exhaust assembly 530. FIG. 21 schematically illustrates an example of the air exhaust assembly 530. The air exhaust assembly 530 includes a first portion 2104 and a second portion 2106. Generally, the first portion 2104 serves as a shoot and is referred to herein as shoot 2104, and the second portion 2106 serves as a scoop and is referred to herein as the scoop 2106. In this example, the shoot 2104 is disposed adjacent to the fan system 708. The shoot 2104 includes a closed outer wall, which may be circular, elliptical, square, rectangular, etc., which encloses an inner cavity. The shoot 2104 is configured to receive air flowing being expelled by the fan system 708, e.g., air flowing from the plenum 602 and over the heat exchanger 706. The shoot 2104 routes the air to approximately an edge 2108 of the rotating frame 506.

The scoop 2106 extends from the shoot 2104 at the edge 2108 of the rotating frame 506 and protrudes into a gap between the rotating frame 506 and a front cover of the imaging system 502. The scoop 2106 includes a first end region 2110 and a second end region 2112, located opposite the first end region 2110 at the edge 2108 of the rotating frame 506. In this example, the first end region 2110 is a leading end in that the first end region 2110 leads the second end region 2112 relative to the rotational direction 606 of the rotating frame 506, and the second end region 2112 is a lagging end in that the second end region 2112 lags or follows the first (leading) end region 2110 relative to the rotational direction 606 of the rotating frame 506.

A side 2114 extends from the first (leading) end region 2110 from the edge 2108 of the rotating frame 506 diagonally towards the second (lagging) end region 2112, away from the rotating frame 506, forming an outlet or opening 2116 at the second (lagging) end region 2112. The opening 2116 provides a path for exhaust air 2118 in the first portion 2104 to expel out of the air exhaust assembly 2102. With this configuration, in one instance air 2120 moving along the side 2114 of the air exhaust assembly 530 and passing the opening 2116 draws the exhaust air 2118 out of the first portion 2104. Additionally, or alternatively, the side 2114 provides a path of the exhaust air 2118 to expel from the air exhaust assembly 530 without resistance from the turbulent air flow.

Figure 22:
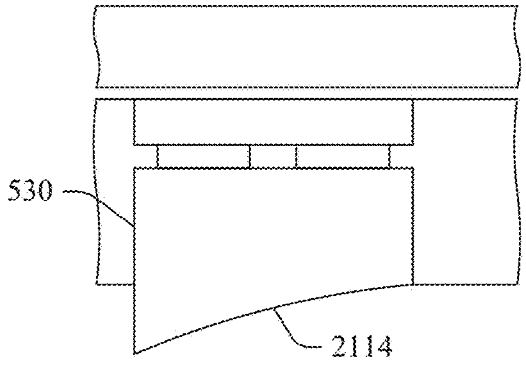
FIG. 22 schematically illustrates an example of the air exhaust assembly with an arc shaped air scoop side, in accordance with an embodiment(s) herein.
Figure 23:
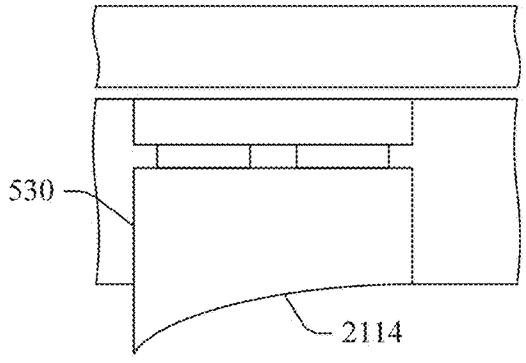
FIG. 23 schematically illustrates an example of the air exhaust assembly with an elliptical shaped air scoop side, in accordance with an embodiment(s) herein.

In FIG. 21, the side 2114 is linear. In another example, the side 2114 is curve shaped. Examples of curves include an arc shape, an elliptical shape, a parabolic shape, etc. FIG. 22 schematically illustrates examples of an arc shaped elongated louver. FIG. 23 schematically illustrates an example of an elliptical shaped elongated louver.

Figure 24:
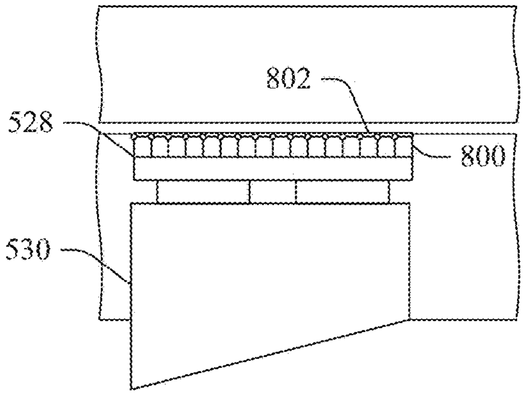
FIG. 24 schematically illustrates an example that includes both the air intake assembly and the air exhaust assembly with the elongated louver of the air intake assembly in the closed position, in accordance with an embodiment(s) herein.
Figure 25:
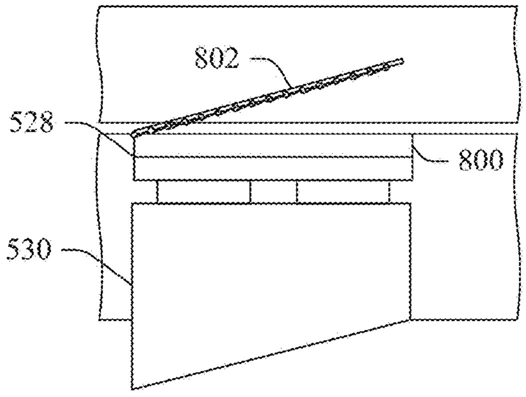
FIG. 25 schematically illustrates an example that includes both the air intake assembly and the air exhaust assembly with the elongated louver of the air intake assembly in the open position, in accordance with an embodiment(s) herein.

FIGS. 24 and 25 schematically illustrate an example that includes both the air intake assembly 528 and the air exhaust assembly 530. In FIG. 24, the elongated louver 802 of the air intake assembly 528 is in the closed position. In FIG. 25, the elongated louver 802 of the air intake assembly 528 is in an open position.

Figure 26:
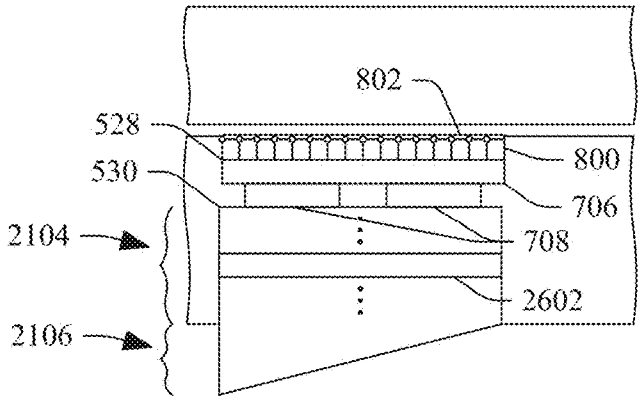
FIG. 26 schematically illustrates an example in which the air exhaust assembly includes a fan system, in accordance with an embodiment(s) herein.

FIG. 26 schematically illustrates an example in which the air exhaust assembly 2102 includes a fan system 2602. In one instance, the fan system 2602 includes a single fan. In another instance, the fan system 2602 includes multiple fans. The fan system 2602 can be disposed anywhere within the air exhaust assembly 530. For example, in one instance the fan system 2602 is disposed adjacent to the fan system 708 and/or the heat exchanger 706. In another instance, the fan system 2602 is disposed in the shoot 2104 adjacent to the scoop 2106. In another instance, the fan system 2602 is disposed between these two positions. Where the fan system 2602 includes more than one fan, in one instance, the fans are aligned with each other, and, in another instance, at least one fan is not aligned with another fan.

Figure 27:
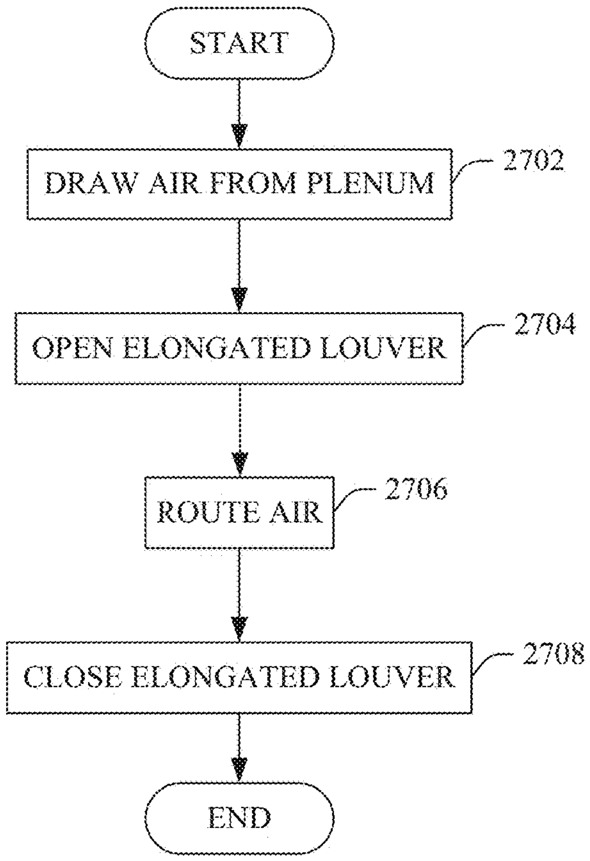
FIG. 27 illustrates an example of a flow chart for a method, in accordance with an embodiment(s) herein.

FIG. 27 illustrates a non-limiting example of a flow chart for a method. It is to be appreciated that the ordering of the acts in one or more of the methods is not limiting. As such, other orderings are contemplated herein. In addition, one or more acts may be omitted, and/or one or more additional acts may be included. At 2702, air from the plenum 602 is drawn over the heat exchanger 706 via the fan system 708, as described herein and/or otherwise. At 2704, turbulent air produced in response to rotating the rotating frame 506 opens the elongated louver 802 of the air intake assembly 528, as described herein and/or otherwise. At 2706, air from the plenum 602 is routed over the heat exchanger 706 by the elongated louver 802 via the path 1002 created by the open elongated louver 802, as described herein and/or otherwise. At 2708, the elongated louver 802 closes in response to the rotating of the rotating frame 506 slowing down or stopping, as described herein and/or otherwise.

Figure 28:
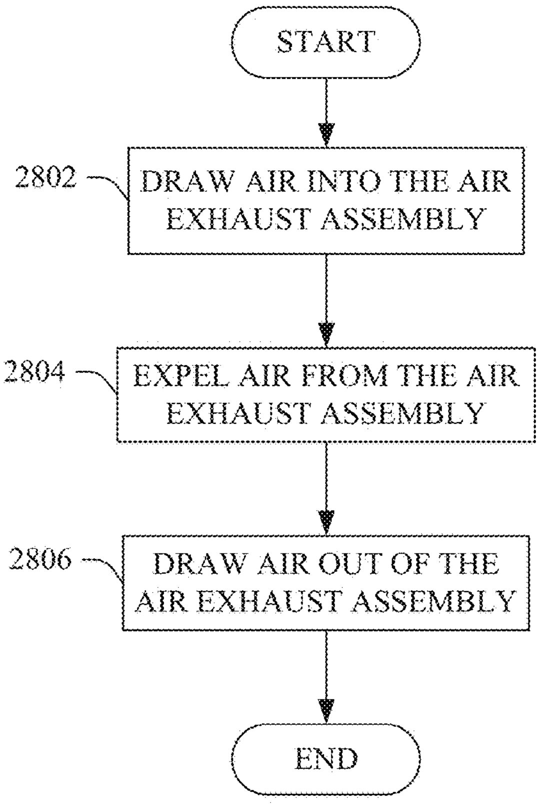
FIG. 28 illustrates another example of a flow chart for another method, in accordance with an embodiment(s) herein.

FIG. 28 illustrates another non-limiting example of a flow chart for a method. It is to be appreciated that the ordering of the acts in one or more of the methods is not limiting. As such, other orderings are contemplated herein. In addition, one or more acts may be omitted, and/or one or more additional acts may be included. At 2802, air from the plenum 602 is drawn over the heat exchanger 706 via the fan system 708 and routed to the air exhaust assembly 530, as described herein and/or otherwise. At 2804, the fan system 708 expels air in a shoot (i.e., the first portion 2104) of the air exhaust assembly 530 through the opening 2116 of the air exhaust assembly 530, as described herein and/or otherwise. At 2806, turbulent air flow produced in response to the rotating the rotating frame further draws air out of the air exhaust assembly 530, as described herein and/or otherwise.

Figure 29:
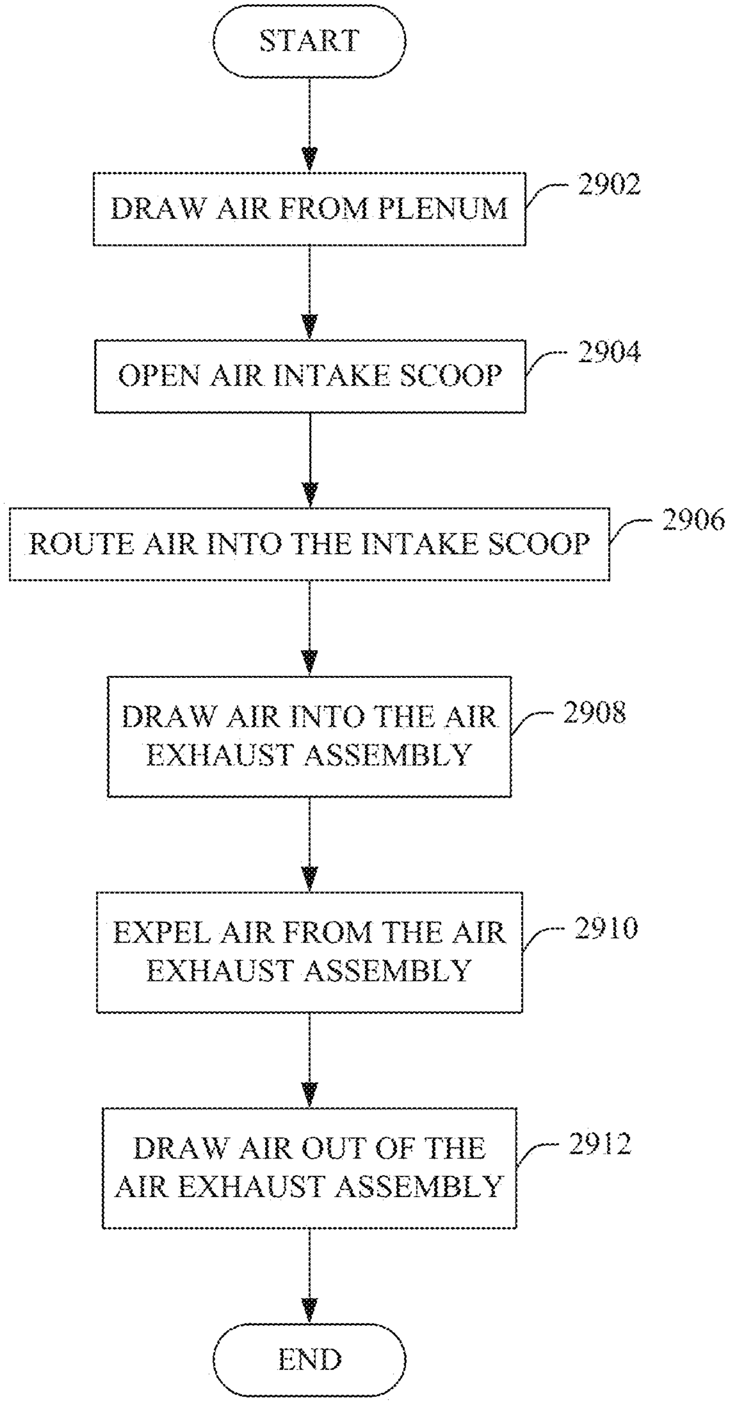
FIG. 29 illustrates an example of a flow chart for a method including the methods of FIGS. 27 and 28, in accordance with an embodiment(s) herein.

FIG. 29 illustrates a non-limiting example of a flow chart for a method that includes the methods of FIGS. 27 and 28. It is to be appreciated that the ordering of the acts in one or more of the methods is not limiting. As such, other orderings are contemplated herein. In addition, one or more acts may be omitted, and/or one or more additional acts may be included. At 2902, air from the plenum 602 is drawn over the heat exchanger 706 via the fan system 708, as described herein and/or otherwise. At 2904, turbulent air produced in response to rotating the rotating frame 506 opens the elongated louver 802 of the air intake assembly 528, as described herein and/or otherwise. At 2906, air from the plenum 602 is forced over the heat exchanger 706 by a scoop created by the open elongated louver 802, as described herein and/or otherwise. At 2908, the air flowing over the heat exchanger 706 is routed to an air exhaust assembly 530, as described herein and/or otherwise. At 2910, the fan system 708 expels air in the shoot 2104 of the air exhaust assembly 530 through the opening 2116 of the air exhaust assembly 530, as described herein and/or otherwise. At 2912, turbulent air flow produced in response to the rotating the rotating frame further draws air out of the air exhaust assembly 530, as described herein and/or otherwise.

In general, the air intake assembly 528 and the air exhaust assembly 530 utilize rotating motion of the rotating frame 506 to facilitate pulling and pushing more air through heat exchanger 706. As discussed herein, the approach described herein can improve an efficiency with drawing in cooling air and/or expelling heated air, relative to a configuration in which the air intake assembly 528 and the air exhaust assembly 530 are omitted. By way of non-limiting example, in one instance employing the air intake assembly 528 while the rotating the rotating frame 506 increased air speed by approximately 25% given the same fan speed, relative to a configuration which did not include the air intake assembly 528. By way of another non-limiting example, in one instance employing the air exhaust assembly 530 while the rotating the rotating frame 506 increased air speed by approximately 41% given the same fan speed, relative to a configuration which did not include the air exhaust assembly 530.

The above can be implemented by way of computer readable instructions, encoded, or embedded on the computer readable storage medium, which, when executed by a computer processor, cause the processor to carry out the described acts or functions. Additionally, or alternatively, at least one of the computer readable instructions is carried out by a signal, carrier wave or other transitory medium, which is not computer readable storage medium.

As used herein, an element or step recited in the singular and proceeded with the word “a” or “an” should be understood as not excluding plural of said elements or steps, unless such exclusion is explicitly stated. Furthermore, references to “one embodiment” of the present invention are not intended to be interpreted as excluding the existence of additional embodiments that also incorporate the recited features. Moreover, unless explicitly stated to the contrary, embodiments “comprising,” “including,” or “having” an element or a plurality of elements having a particular property may include such additional elements not having that property. The terms “including” and “in which” are used as the plain-language equivalents of the respective terms “comprising” and “wherein.” Moreover, the terms “first,” “second,” and “third,” etc. are used merely as labels, and are not intended to impose numerical requirements or a particular positional order on their objects.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term “computer” or “module” may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term “computer”. The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms “software” and “firmware” are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present disclosure. That is, features of the described embodiments can be combined with any appropriate aspect described above and optional features of any one aspect can be combined with any other appropriate aspects. Similarly, features set forth in dependent claims can be combined with non-mutually exclusive features of other dependent claims, particularly where the dependent claims depend on the same independent claim. Single claim dependencies may have been used as practice in some jurisdictions that require them, but this should not be taken to mean that the features in the dependent claims are mutually exclusive.

What is claimed is:

1. A computed tomography imaging system, comprising:
- a gantry;
- a rotating frame rotatably supported in the gantry, the rotating frame, including:
  - an X-ray source configured to emit X-ray radiation that traverses an examination region; and
  - an X-ray radiation sensitive detector disposed opposite the X-ray source and configured to detect X-ray radiation traversing the examination region and generate signals indicative of the detected X-ray radiation;
- a plenum configured to hold pressurized air;
- a cooling system, disposed on the rotating frame, the cooling system including:
  - a heat exchanger configured to transfer heat from a coolant cooling at least one component carried by the rotating frame, and
  - a fan system configured to move cool air from the plenum to the heat exchanger and move heated air away from the heat exchanger, wherein the cooling system further includes:
    - an air intake assembly configured to provide an air intake path for the cool air to the heat exchanger, wherein the air intake assembly includes:
      - a shoot;
      - a mechanical bearing affixed to one end of the shoot; and
      - an elongated louver with a first end affixed to the mechanical bearing; and
    - an air exhaust assembly configured to provide an air exhaust path for the heated air.

2. The computed tomography imaging system of claim 1, wherein air intake assembly is disposed between the plenum and the heat exchanger.

3. The computed tomography imaging system of claim 1, wherein the air exhaust assembly includes:
- a shoot disposed adjacent to the heat exchanger; and
- a scoop with a first side and a second side, wherein the first side is at an edge of the rotating frame and the second side protrudes off of the rotating frame into a space between the rotating frame and a stationary frame of the gantry.

4. The computed tomography imaging system of claim 1, wherein the elongated louver is configured to pivot about the mechanical bearing from a closed position to an open position in response to receiving air produced while rotating the rotating frame, forming a scoop that routes air from the plenum to the heat exchanger.

5. The computed tomography imaging system of claim 4, wherein the elongated louver includes a plurality of slats configured in a normally open position to allow air to flow through channels of the elongated louver when the rotating frame is not rotating.

6. The computed tomography imaging system of claim 5, wherein the plurality of slats are configured to automatically close the channels in response to the air produced when the rotating frame is rotating.

7. The computed tomography imaging system of claim 1, wherein the heat exchanger includes a first side adjacent to the plenum and a second side adjacent to the air exhaust assembly.

8. A computed tomography imaging system, comprising:
- a gantry;
- a rotating frame rotatably supported in the gantry, the rotating frame, including:
  - an X-ray source configured to emit X-ray radiation that traverses an examination region; and
  - an X-ray radiation sensitive detector disposed opposite the X-ray source and configured to detect X-ray radiation traversing the examination region and generate signals indicative of the detected X-ray radiation;
- a plenum configured to hold pressurized air;
- a cooling system, disposed on the rotating frame, the cooling system including:
  - a heat exchanger configured to transfer heat from a coolant cooling at least one component carried by the rotating frame, and
  - a fan system configured to move cool air from the plenum to the heat exchanger and move heated air away from the heat exchanger, wherein the cooling system further includes:
    - an air intake assembly configured to provide an air intake path for the cool air to the heat exchanger; and
    - an air exhaust assembly configured to provide an air exhaust path for the heated air, wherein the air exhaust assembly includes:
    - a shoot disposed adjacent to the heat exchanger; and
    - a scoop with a first side and a second side, wherein the first side is at an edge of the rotating frame and the second side protrudes off of the rotating frame into a space between the rotating frame and a stationary frame of the gantry.

9. The computed tomography imaging system of claim 8, wherein the scoop includes a third side that extends diagonally from the edge of the rotating frame to the space, and the second side includes an air outlet.

10. The computed tomography imaging system of claim 9, wherein the air outlet faces a direction opposite of a rotation direction of the rotating frame.

11. A method, comprising:

receiving, at an air intake assembly of a cooling system disposed on a rotating frame of a gantry of a computed tomography imaging system, turbulent air produced in response to rotating the rotating frame of the gantry of the computed tomography imaging system, wherein air intake assembly includes a shoot, a mechanical bearing affixed to one end of the shoot, and an elongated louver with a first end affixed to the mechanical bearing;

opening the elongated louver of the air intake assembly with the turbulent air, wherein the open elongated louver provides an air intake scoop; and routing, with the air intake scoop and a fan system of the computed tomography imaging system, air from a plenum of the computed tomography imaging system to a heat exchanger of the computed tomography imaging system, providing a first flow of air.

12. The method of claim 11, further including:

closing the elongated louver of the air intake assembly in an absence of the turbulent air.

13. The method of claim 12, further including:

drawing, with the fan system, air from the plenum to the heat exchanger through channels in the elongated louver in the absence of the turbulent air, providing a second flow of air, wherein the first flow of air is greater than the second flow of air.

14. The method of claim 11, further including:

receiving, at a shoot of an air exhaust assembly of the computed tomography imaging system, air flowing over the heat exchanger; and routing, with the shoot, the received air to a scoop of the air exhaust assembly.

15. The method of claim 14, further including:

expelling, with the scoop and the fan system, the received air from the air exhaust assembly.

16. A method, comprising:

receiving, at a shoot of an air exhaust assembly of a cooling system disposed on a rotating frame of a gantry of a computed tomography imaging system, air flowing over a heat exchanger of the computed tomography imaging system, wherein the cooling system further includes a shoot disposed adjacent to the heat exchanger and a scoop with a first side and a second side, wherein the first side is at an edge of the rotating frame and the second side protrudes off of the rotating frame into a space between the rotating frame and a stationary frame of the gantry;

routing, with the shoot, the received air to the scoop of the air exhaust assembly; and expelling, with the scoop and a fan system of the air exhaust assembly, the air received in the shoot from the air exhaust assembly.

17. The method of claim 16, wherein expelling the air received includes routing the air off of the rotating frame of the gantry of the computed tomography imaging system.

18. The method of claim 16, further including:

receiving, at an air intake assembly of the cooling system, turbulent air produced in response to rotating the rotating frame of the gantry of the computed tomography imaging system, automatically opening an elongated louver of the air intake assembly with the turbulent air, wherein the open elongated louver provides an air intake scoop; and routing, with the air intake scoop and a fan system disposed in of the computed tomography imaging system, air from a plenum of the computed tomography imaging system to a heat exchanger of the computed tomography imaging system.

19. The method of claim 18, further including:

closing the elongated louver of the air intake assembly in an absence of the turbulent air.

20. The method of claim 19, further including:

drawing, with the fan system, air from the plenum to the heat exchanger through channels in the elongated louver in the absence of the turbulent air.

* * * * *